United States Patent [19]

Egger et al.

[11] Patent Number: Plant 7,493

[45] Date of Patent: Apr. 9, 1991

[54] **GAZANIA PLANT CALLED *GAZANIA RIGENS* 'MOORPARK ORANGE'**

[75] Inventors: Janet N. Egger, Ventura; Stephen H. Beimel, Agoura, both of Calif.

[73] Assignee: Mitsuwa Nursery, Inc., Moorpark, Calif.

[21] Appl. No.: 337,072

[22] Filed: Apr. 12, 1989

[51] Int. Cl.[5] ..... A01H 5/00

[52] U.S. Cl. ..... Plt./68

[58] Field of Search ..... Plt./68

[56] References Cited

PUBLICATIONS

Brickell, C. ed. et al., 1980, "International Code of Nomenclature for Cultivated Plants"—1980, Bohn, Schelterra & Holkema, Utrecht, dr. w. Junk b.v., Publishers, The Hague, pp. 19–20.

*Primary Examiner*—Howard J. Locker

*Attorney, Agent, or Firm*—Roylance, Abrams, Berdo & Goodman

[57] ABSTRACT

A perennial hybrid Gazania groundcover which is distinguished by the deep orange color of its flowers and its green trailing foliage. In addition, the invention plant is floriferous, vigorous, and disease and frost tolerant.

1 Drawing Sheet

BACKGROUND OF THE INVENTION

The present invention relates to a new and distinctive cultivar of Gazania plant botanically known as *Gazania rigens* hybrid and referred to commercially by the cultivar name 'Moorpark Orange'. *Gazania rigens* 'Moorpark Orange' was discovered in the mother stock field of Mitsuwa Nursery in Moorpark, Calif. It originated as a natural hybrid. Its exact parents are unknown, but are in the *Gazania rigens* and *Gazania rigens* var. leucoleana groups.

BRIEF DESCRIPTION OF THE INVENTION

*Gazania rigens* 'Moorpark Orange' is a perennial trailing groundcover with good vigor, hardiness, deep green leaves and deep orange flowers that bloom from February to December in Southern California. The dark orange color of the flowers is unique in the trailing green leaf Gazania groundcovers and is believed to be a substantial step forward in the groundcover industry.

DESCRIPTION OF THE DRAWING

The accompanying color photograph, forming a part of this disclosure, was taken in Summer 1988 in a greenhouse in Moorpark, Calif., and shows a close-up of *Gazania rigens* 'Moorpark Orange' growing in a flat; the view being more or less straight down onto the plants. The photograph shows the typical flower and foliage form and color as true as is reasonably possible in this type of color photograph.

Comparison of *Gazania rigens* 'Moorpark Orange' with other Commercial Orange Gazania Groundcovers The primary distinguishing feature of *Gazania rigens* 'Moorpark Orange' is the deep orange color of its flowers. This color is new to the green leaf trailing Gazania groundcovers. That is, to the inventors' knowledge, *Gazania rigens* 'Moorpark Orange' is the first Gazania with deep orange flowers, green leaves, and a trailing habit. There are other deep orange flowering Gazania groundcovers but they have grey foliage and/or clumping habits.

To the inventors' knowledge, the only other orange flowering Gazania with a trailing habit and green foliage has light orange flowers. This is *Gazania rigens* 'Mitsuwa Orange', 'Mitsuwa Orange' is described and claimed in U.S. Plant Pat. No. 5,796, issued Nov. 4, 1986, and owned in common with the present invention.

Compared to *Gazania rigens* 'Mitsuwa Orange', *Gazania rigens* 'Moorpark Orange' is more vigorous and its leaves are a deeper green. The flower heads are larger, with a darker orange color, and with a black ring around the flower center. Both are very floriferous. *Gazania rigens* 'Moorpark Orange' is more frost hardy.

DETAILED DESCRIPTION

The following is detailed description of *Gazania rigens* 'Moorpark Orange' based on plants produced under commercial practices outdoors at Mitsuwa Nursery, Moorpark, Calif. Color references are made to The Royal Horticultural Society Colour Chart except where the context indicates a term having its ordinary dictionary meaning.

Parentage: A natural hybrid within the *Gazania rigens* and the *Gazania rigens* var. leucoleana groups.

Plant form: Plants are a vigorous growing, trailing groundcover.

Habit of growth: Plants are decumbent, spreading rapidly to approximately 1 meter in diameter. Plants form a dense carpet to approximately 13 cm in height.

Foliage: Foliage is a medium green with simple alternate leaves.

(1) *Size.*—Mature leaves are approximately 6–10 cm in length and 1 cm in width at the widest point.

(2) *Shape.*—Oblanceolate.

(3) *Texture.*—The top side of the leaf is glabrous, the bottom side is densely white tomentose.

(4) *Margin.*—Subrevolute.

(5) *Color.*—Young foliage, top side — 137 C. Young foliage, underside — 155 D. Mature foliage, top side — 137 A & B. Mature foliage, underside — 155 D.

FLOWERING DESCRIPTION

1. General: The flowers are a deep orange with a black ring around the flower center at the base. The plants are very floriferous.
2. Habit: The flower heads arise from leaf axils on peduncles to approximately 15 cm in length.
3. Season of bloom: Varies with the climate. In Moorpark, Calif., heavy bloom occurs from approximately late February to early December.
4. Flower Parts: (a) Flower heads measures 5–6 cm across. (b) Ray petals measure up to 4 cm. in length. The base of each petal has a black oval shaped spot measuring approximately 3 mm across with 3 white dots in the middle. This black oval shaped spot forms the band or ring at the flower base. The underside of each ray petal has a dark section down the center between the two main veins. (c) There are 18–22 ray petals per flower head.
5. Color:

*Disc flower (closed).*—25 B.
   *Ray petal, topside tip.*—23 A.
   *Ray petal, middle to spot.*—25 A.
   *Ray petal, spot.*—202 A.
   *Ray petal, bottomside edges.*—24 A.
   *Ray petal, bottomside dark section.*—117 A.

Disease Resistance: No disease problems noted. In the fields at Mitsuwa Nursery, *Gazaina rigens* 'Moorpark Orange' has proven to be disease tolerant.

Hardiness: In the winter of 1987 the Gazania trial fields in Moorpark, Calif. were badly frost damaged. Many of the Gazania varieties died and most died back. Almost all had leaf burn. *Gazania rigens* 'Moorpark Orange' had no foliage die back and minimal leaf burn; it fared much better than other Gazania varieties in the same field. It is much hardier than Mitsuwa Yellow, Mitsuwa Orange, and Mitsuwa White, all of which has some foliage die back.

Propagation: Asexual reproduction by stem cuttings has shown that the unique features of this new Gazania are stable and are reproduced true to type in successive propagations. *Gazania rigens* 'Moorpark Orange' roots in 2–4 weeks under warm conditions.

We claim:

1. A new and distinct cultivar of Gazania as described and illustrated, particularly characterized by its floriferous showy deep orange flowers, green foliage, vigorous growth, and trailing habit.

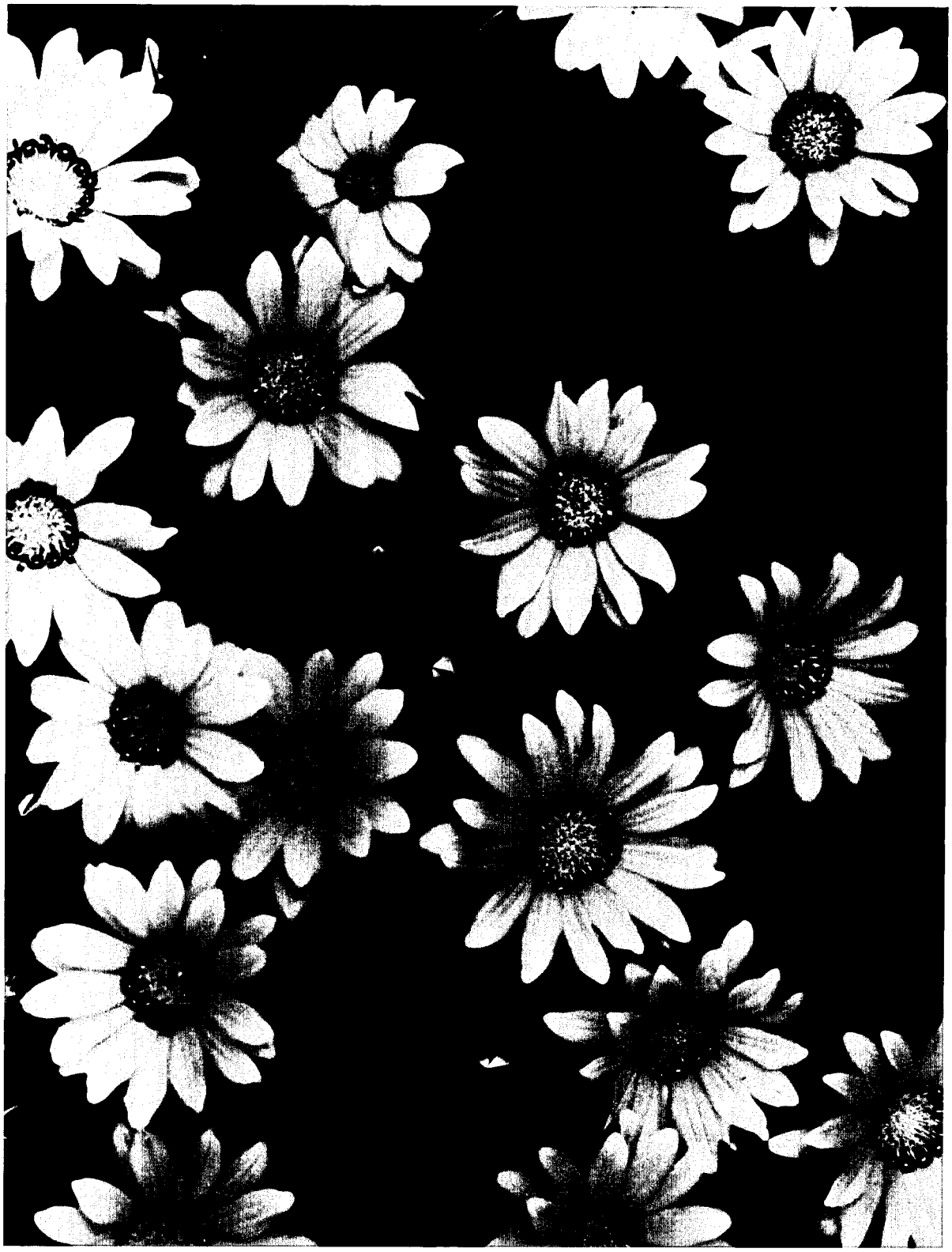

* * * * *